United States Patent [19]

Lecloux et al.

[11] Patent Number: 5,086,189

[45] Date of Patent: Feb. 4, 1992

[54] PROCESS FOR THE MANUFACTURE OF EPOXIDES

[75] Inventors: André Lecloux, Meise; Claude Declerck, Brussels; Franz Legrand, Quaregnon, all of Belgium

[73] Assignee: Interox (Société Anonyme), Brussels, Belgium

[21] Appl. No.: 474,226

[22] Filed: Feb. 2, 1990

Related U.S. Application Data

[63] Continuation of Ser. No. 649,959, Sep. 11, 1984, abandoned, which is a continuation of Ser. No. 517,387, Jul. 27, 1983, abandoned, which is a continuation of Ser. No. 391,407, Jun. 23, 1982, abandoned.

[30] Foreign Application Priority Data

Jun. 26, 1981 [FR] France .................... 81 12797

[51] Int. Cl.$^5$ ........................... C07D 301/12
[52] U.S. Cl. ........................... 549/531
[58] Field of Search ........................... 549/531

[56] References Cited

U.S. PATENT DOCUMENTS

| 2,833,787 | 5/1958 | Carlson et al. | 549/531 |
| 3,122,569 | 2/1964 | Kaman | 549/521 |
| 3,293,269 | 12/1966 | Wolgemuth | 549/531 |
| 3,778,451 | 12/1973 | Poite | 549/531 |
| 3,993,673 | 11/1976 | McMullen | 549/531 |
| 4,242,285 | 12/1980 | Renga | 549/531 |
| 4,290,960 | 9/1981 | Ross et al. | 549/531 |

FOREIGN PATENT DOCUMENTS

| 2803757 | 8/1978 | Fed. Rep. of Germany | 549/531 |
| 2803791 | 8/1978 | Fed. Rep. of Germany | 549/531 |
| 1201458 | 12/1959 | France . | |
| 1506459 | 12/1967 | France . | |
| 2082811 | 12/1971 | France | 549/531 |
| 13331 | 5/1970 | Japan | 549/531 |
| 19894 | 7/1970 | Japan | 549/531 |
| 19899 | 7/1970 | Japan | 549/531 |

OTHER PUBLICATIONS

*Advanced Inorganic Chemistry*, F. Albert Cotton and G. Wilkinson, Interstate Publishers, 1962, pp. 372–373, 404–405.

*CRC Handbook of Chemistry and Physics*, 53rd Edition, Published by The Chemical Rubber Co., 1972–1973, pp. D117–D119.

"Epoxidation of Eight- and Twelve-Membered Cyclic Olefins with Hydrogen Peroxide in the Presence of Metal Oxide Catalysts", Itakura et al, Bulletin of the Chemical Society of Japan, vol. 42, pp. 1604–1608, (1969).

English translation of German Patent No. 2,803,791.
English translation of German Patent No. 2,803,757.
English translation of Japanese patent application 45-13331.
English translation of Japanese patent application 45-19894.
English translation of Japanese patent application 45-19899.

Paul A. Grieco et al, J. Org. Chem., vol. 42 (No. 11) (1977) pp. 2034–2036.

Hans J. Reich et al, Synthesis (Apr. 1978) pp. 299–301.

T. Hori et al, J. Org. Chem., vol. 43, No. 9 (1978) pp. 1689–1697.

M. Pralus et al, Fundamental Research in Homogeneous Catalysis, vol. 3 (1979), edited by M. Tsutsui, Plenum Press, pp. 327–343.

*Primary Examiner*—Richard L. Raymond
*Assistant Examiner*—M. W. Russell
*Attorney, Agent, or Firm*—Spencer & Frank

[57] ABSTRACT

Epoxides are manufactured by reacting olefines, such as cyclohexene, isoamylene, alpha-pinene, allyl alcohol, 2,5-dihydrofuran and styrene, with hydrogen peroxide, in a homogeneous liquid reaction mixture containing less than 10% by weight of water, in the presence of a compound of a metal of group 6a, such as selenium dioxide or selenous acid, and of an organic nitrogen-containing base having a pKa of not more than 8, such as pyridine, chloropyridine, collidine, quinoline, isoquinoline or a lutidine.

21 Claims, 1 Drawing Sheet

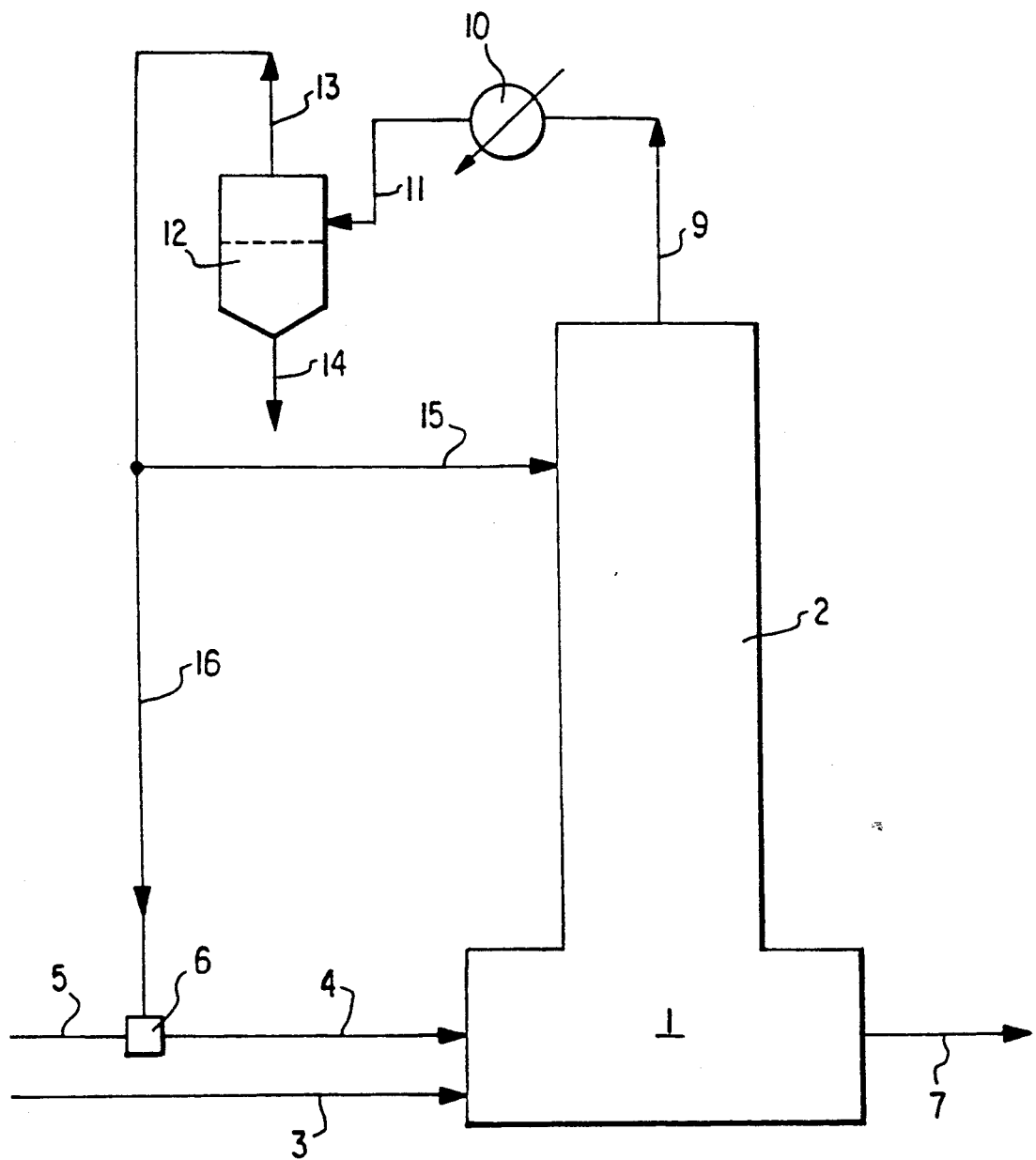

PROCESS FOR THE MANUFACTURE OF EPOXIDES

This application is a continuation of application Ser. No. 06/649,959, filed Sept. 11, 1984 now abandoned, which is a continuation of application Ser. No. 06/517,387 filed July 27th, 1983 now abandoned, which is a continuation of application Ser. No. 06/391,407 filed June 23rd, 1982, now abandoned.

BACKGROUND OF THE INVENTION

The present invention relates to a process for the manufacture of epoxides by reacting hydrogen peroxide with a compound containing an ethylenic double bond, in the presence of a catalyst.

Epoxides are products having numerous industrial applications, for example in the manufacture of thermosetting polymers which can be used, in particular, as adhesives or surface coatings. Industrially, epoxides are generally manufactured in accordance with complex processes, such as the dehydrochlorination of the corresponding chlorohydrins or the catalytic oxidation of olefines with hydroperoxides or directly with molecular oxygen. To reduce the manufacturing costs and the formation of by-products, and to simplify the processes, it has been proposed to manufacture epoxides by reacting hydrogen peroxide directly with the corresponding olefine in the liquid phase, by virtue of the use of certain specific catalysts. However, the processes known hitherto all have various disadvantages. The productivity of the reactors is low because the reaction is too slow or the solutions to be used are too dilute, the catalysts have an insufficient life and are rapidly deactivated, or the selectivity is poor and many undesirable by-products are obtained, such as diols or alkoxyalcohols, or the separation of the reaction products is difficult. Furthermore, the hydrogen peroxide must frequently be used in the anhydrous form and the reaction mixture must be kept anhydrous. In addition, certain catalysts have an activity which depends greatly on the olefine to be epoxidised. Thus, if selenium oxide is used as the catalyst, diols are obtained with olefines such as cyclohexene, and epoxides are only obtained with very complex olefines of the macrocyclic type (J. Itakura et al., Bull. of the Chem. Soc. of Japan, 1969, 42, pages 1,604 to 1,608).

SUMMARY OF THE PRESENT INVENTION

The object of the present invention is to overcome the disadvantages of the known processes and to provide a process which gives a high selectivity in respect of epoxide, with a good productivity.

For this purpose, the invention relates to a process for the manufacture of epoxides, in which hydrogen peroxide is reacted with a compound containing an ethylenic double bond, in a homogeneous liquid reaction mixture containing a catalyst and a base, and in which the concentration of water in the reaction mixture is kept below 10% by weight, a base is used which is chosen from amongst organic nitrogen-containing bases having a pKa of not more than 8, and a catalyst is used which is chosen from amongst the metals of group 6a of the Periodic Table of the Elements and their compounds.

DETAILED DESCRIPTION OF THE PRESENT INVENTION

The catalysts used in the process according to the invention are metals and compounds of the metals of group 6a of the Periodic Table of the Elements (international classification). Compounds of selenium and tellurium are preferred. The best results have been obtained with selenium compounds. In these compounds, the metals can have different oxidation states. Preferably, compounds are used in which the metals are in an oxidation state below the maximum oxidation state.

The metal compounds used as catalysts are generally chosen from amongst compounds which are soluble in the reaction mixture at the concentrations used. They can be of organic or inorganic type. Thus, inorganic compounds which can be used are oxides, mixed oxides, hydroxides, various salts, such as halides and oxyhalides, and also anhydrides, heterpolyacids and acids and the corresponding salts. Organic compounds which can be used are esters of the mineral acids derived from these metals, organic acids of these metals and also organometallic compounds of these metals, such as the metal carbonyls.

The oxides, acids (and corresponding esters), anhydrides and organic acids of these metals has given good results. The best results have been obtained with selenium dioxide and selenous acid.

The catalysts are generally used in amounts of more than 0.01 g, most frequently of more than 0.05 g and preferably of more than 0.1 g per liter of reaction mixture. These amounts do not generally exceed 25 g and preferably 10 g per liter.

The catalysts can be added to the reaction mixture in the pure state or in the form of a solution in one of the constituents of the reaction mixture.

The organic nitrogen-containing bases used in the process according to the invention have a pKa, in water, which does not exceed 8 and preferably 7.5. Inactivation of the catalyst and inhibition of the reaction are thus avoided in particular. In general, the pKa of the base used is at least 2 and preferably at least 2.5. Bases having a lower pKa can nevertheless be used, but in this case, they must be used in larger amounts. The best results have been obtained with bases having a pKa of between 2.5 and 7.5. The base used must also preferably be inert towards the hydrogen peroxide under the reaction conditions. It is possible to use a single base or a mixture of bases.

Suitable bases are those which are inert towards the hydrogen peroxide under the reaction conditions and which contain, in their structure, a ring of aromatic character, such as pyridine, its halogeno derivatives, its amino derivatives, such as 2-aminopyridine, 3-aminopyridine and 2,5-diaminopyridine, its alkoxy derivatives, such as 3-methoxypridine and 4-methoxypridine, and its alkyl derivatives, such as picolines, lutidines (2,3-, 2,4-, 2,5-, 2,6-, 3,4-, 3,5-, and 3,6-), collidines, ethylpyridines and propylpyridines, N-alkyl derivatives of aniline, such as N-methylaniline, N,N-dimethylaniline, N-ethylaniline and N,N-diethylaniline, N-methyltoluidines, N,N-dimethyltoluidines, N-ethyltoluidines, N-allylamine, quinoline and isoquinoline and their derivatives, such as 1-aminoisoquinoline, 3-aminoquinoline, methylquinolines, dimethylquinolines and 6-methoxyquinoline, imidazole and its derivatives, such as 1-methylimidazole, and also benzimidazole and its derivatives, such as 2-methylbenzimidazole, 2-ethylbenzimidazole and 2-phenylbenzimidazole. Pyridine, chloropyridine, quinoline and isoquinoline, and also their derivatives substituted by one or more alkyl groups containing 1 or 2 carbon atoms per alkyl group, are very particularly suitable. Good results have been obtained with pyridine, chloropyridine, collidine, quinoline, isoquinoline and lutidines. One or more bases can be used.

The bases can be used in variable amounts. In general, at least 0.01 mol of base is added to the reaction mixture per gram atom of metal in the catalyst. In general, the amount of base used does not exceed 20 mols and most frequently 10 mols per gram atom of metal. Good results have been obtained with amounts of between 0.1 and 10 mols and preferably of between 0.3 and 6 mols of base per gram atom of metal in the catalyst. The total amount of base present in the reaction mixture does not generally exceed 4% of the weight of the latter.

The compounds containing an ethylenic double bond, which can be used as reactants in the process according to the invention, can be of very diverse types. These olefines contain one or more ethylenic double bonds $>C=C<$. They can be aliphatic, alicyclic or aromatic. They can optionally contain, in their main chain, one or more heteroatoms generally chosen from amongst nitrogen, sulphur or oxygen atoms. They can be substituted by various atoms or groups which are stable in the reaction mixture, such as halogens, and more particularly chlorine, fluorine or bromine atoms, or hydroxyl, alkoxy, nitro, amino, carbonyl, nitrile, acid, ester or amide groups, or alternatively by aromatic, aliphatic or alicyclic groups which are themselves optionally substituted. In general, they contain from 2 to 40 carbon atoms.

The process according to the invention is generally applied to olefines corresponding to the general formula:

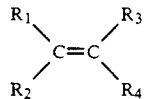

in which $R_1$, $R_2$, $R_3$ and $R_4$ represent identical or different atoms or groups chosen from amongst hydrogen, halogens, and more particularly chlorine, fluorine or bromine, substituted or unsubstituted alkyl, cycloalkyl or aryl groups optionally containing one or more hetero-atoms in their structure, and ether, acid, ester, nitrile or amide groups, or in which $R_1$ and $R_2$ or $R_3$ and $R_4$ represent, in pairs, a substituted or unsubstituted alkyl chain optionally containing one or more hetero-atoms, or in which $R_1$ and $R_3$ or $R_2$ and $R_4$ represent, in pairs, a substituted or unsubstituted alkyl chain optionally containing one or more hetero-atoms.

Examples which may be mentioned of olefines of these types are propylene, but-1-ene, but-2-ene, isobutene, butadiene, pentenes, and in particular pent-1-ene, 2-methylbut-1-ene, 3-methylbut-1-ene, 2-methylbut-2-ene, piperylene, hex-1-ene, hex-2-ene and hex-3-ene, hexadienes, 2,3-dimethyl-but-2-ene, hept-1-ene, 3-ethylpent-2-ene, oct-1-ene, diisobutylene, 2,4,4-trimethylpent-1-ene and 2,4,4-trimethylpent-2-ene, octadienes, non-1-ene, dec-1-ene, undec-1-ene, dodec-1-ene, tridec-1-ene, tetradec-1-ene, pentadec-1-ene, hexadec-1-ene, heptadec-1-ene, octadec-1-ene, nonadec-1-ene, eicos-1-ene, propylene trimers and tetramers, polybutadienes, isoprene, terpenes, such as terpinenes, limonene, terpinolene, sabinene, pinene, camphene, myrcene, cadinene, cedrene, santalene, calarene, colophene and polyterpenes and also their derivatives, such as geraniol, linalol and linalyl acetate, methylenecyclopropane, cyclopentene and its derivatives substituted by alkyl or aryl groups, cyclopentadiene, cyclohexene and its derivatives substituted by alkyl and aryl groups, methylenecyclopentane, cyclohexadiene, methylenecyclohexane, norbornene, cycloheptene, vinylcyclohexane, vinylcyclohexene, styrene, cyclooctene, cyclooctadienes, vinylnorbornene, substituted or unsubstituted indene, tetrahydroindene, alpha-methylstyrene and alpha-alkylstyrenes optionally substituted on the aromatic nucleus, dicyclopentadiene, divinylbenzene, substituted or unsubstituted dihydronaphthalenes, cyclododecene, cyclododecatriene, stilbene, 2,3-diphenylbut-2-ene, diphenylbutadiene, vitamin A, beta-carotene, vinylidene fluoride, allyl chloride and bromide, trichloropropylenes, crotyl chloride, methallyl chloride, chlorobutenes, dichlorobutenes, dibromobutadienes, dichlorobutadienes, hexafluorobutadiene, allyl alcohol and methallyl alcohol and also their alkyl or aryl derivatives, but-1-en-4-ol and its 2-alkyl and 4-alkyl derivatives, but-2-en-1-ol, but-2-ene-1,4-diol, cyclopentenediols, pent-4-enols, 2-methylpent-2-en-1-ol, 1,2-dihydroxy-4-vinylbenzene, beta-chlorostyrene and alpha-alkyl-beta-chlorostyrenes optionally substituted on the aromatic nucleus, octa-2,7-dien-1-ol, cyclohexylcarbinol, tridec-2-en-1-ol, 2- and 3-alkoxypropenes and 2- and 3-aryloxypropenes and their substituted derivatives, unsaturated steroids, ethoxyethylene, diallyl ether and its substituted derivatives, isoeugenol, anithole, isosafrole, dihydrofuran and its alkyl derivatives, benzofuran and its substituted derivatives, unsaturated carboxylic acids of all types, such as acrylic acid, methacrylic acid, alpha- and beta-cyanoacrylic acids and their derivatives, crotonic acid, maleic acid and its alkyl derivatives, vinylacetic acid and unsaturated fatty acids, including, more particularly, oleic, linoleic, palmitoleic, linolenic, vaccinic, gadoleic, ricinoleic and eleostearic acids, and natural fats and oils in which they are present, and also esters of all these unsaturated acids, such as alkyl acrylates and methacrylates, diallyl maleate, methyl 7-hydroxyhept-5-enoate and methyl oleate, and esters of unsaturated alcohols, such as allyl carbonate, diallyl phthalate and allyl acetate.

The process according to the invention is particularly suitable for epoxidising acyclic or cyclic olefines containing not more than 6 carbon atoms per ring. It is very particularly suitable for epoxidising olefines containing from 2 to 20 carbon atoms, and more especially internal olefins (that is to say cyclic compounds which contain at least one ethylenic double bond in a ring) which are optionally substituted, and substituted alkenes.

Good results have been obtained in the epoxidation of cyclohexene, 2-methylbut-2-ene, styrene, allyl chloride, alpha-pinene, allyl alcohol and dihydrofuran.

The hydrogen peroxide can be used in the form of an aqueous solution or in the form of an organic solution. For economic reasons, it is generally used in the form of an aqueous solution. Solutions containing at least 20% and preferably at least 30% of hydrogen peroxide are suitable. For reasons of availability, the solutions used do not generally contain more than 95% and most frequently not more than 90% of hydrogen peroxide.

The reaction can be carried out with molar ratios of olefine to hydrogen peroxide in the reaction mixture which can vary within wide limits. In general, it is preferred to use molar ratios of at least 0.9 in order to ensure a good selectivity. Most frequently, this molar ratio is more than 1.5. In general, the molar ratio is less than 10 and preferably less than 5 for economic reasons, so that it is not necessary to recycle excessive amounts of unconverted olefines. Good results have been obtained with molar ratios of the order 3.

The reaction conditions are chosen so as to give a homogeneous mixture. To do this, it is advantageous to use an organic solvent. The use of an organic solvent is less advantageous if the olefine is capable of solubilising the hydrogen peroxide, the epoxide and the catalyst at the concentrations used. This frequently applies if the olefine contains ether groups or hydroxyl or carboxyl groups in its structure, as is the case, for example, of unsaturated alcohols, such as allyl alcohol, unsaturated esters and unsaturated acyclic or cyclic ethers, such as dihydrofuran. In this case, it may be necessary to use a large excess of olefine to epoxidised, whereby the molar ratio of olefine to hydrogen peroxide can be as much as 30.

If an organic solvent is used, it is preferably chosen so as to solubilise the olefine, the hydrogen peroxide, the epoxide and the catalyst at the concentrations used. Moreover, the solvent must be inert towards the reactants used, under the reaction conditions. It is possible to use a single solvent or a mixture of solvents. The solvent is generally chosen from amongst alcohols, cyclic ethers and esters containing from 2 to 12 carbon atoms and preferably from 3 to 8 carbon atoms. It is preferred to use primary, secondary or tertiary alcohols. Most frequently, the solvent used is chosen from amongst ethanol, n-propanol, isopropanol, butan-1-ol, butan-2-ol, tert.-butanol, amyl alcohol, isoamyl alcohol, tert.-amyl alcohol, cyclohexanol, benzyl alcohol, heptan-1-ol and hexanol. Good results have been obtained with benzyl alcohol and n-butanol.

The solvent can be used in variable amounts. In general, the reaction mixture contains at least 20% by weight of solvent, in order to prevent the formation of two liquid phases, either before the reaction or during the reaction. In general, the amount of solvent does not exceed 90% of the mixture, so as to simplify the separation operations and so as not to have too great a reduction in reaction rates as a result of dilution. The reaction mixture preferably contains from 30 to 80% by weight of solvent. Good results have been obtained when the molar ratio of olefine to solvent is of the order of 1.

The water contained in small amounts in the reaction mixture is generally the water formed by the reaction or the water introduced with the reactants. Preferably, the amount of water present is kept below 5% of the weight of the reaction mixture.

Other additives, such as stabilisers for the hydrogen peroxide, polymerisation inhibitors or, if appropriate, inorganic or organic derivatives capable of fixing the water of the reaction medium, can also be added to the reaction mixture. These possible additives are generally present in amounts of less than 3% of the weight of the reaction mixture.

The temperature and the pressure at which the reaction is carried out can vary within very wide limits. They are chosen as a function of the nature of the olefine to be epoxidised and so as not to exceed the decomposition temperature of the reaction mixture. The temperature is usually below 150° C. and most frequently between 0° and 120° C. Good results have been obtained at temperatures between 40° and 100° C. The reaction pressure can be less than, equal to or greater than atmospheric pressure. The pressure is generally less than 5 atmospheres. Good results have been obtained using pressures of 0.05 to 3 atmospheres. In general, the temperature and the pressure are adjusted so as to ensure that the reaction mixture boils.

The reaction time depends on the nature of the olefine to be epoxidised and also of the catalyst, the solvent, and the base used. It can range from 1 minute to 50 hours.

The process according to the invention can be carried out continuously or batchwise, in a single reactor or in a number of reactors in parallel or in series. To carry out the process according to the invention, it is possible to use any equipment suitable for liquid reaction mixtures.

The catalysts, the bases and the reactants can be introduced in various ways which are in themselves known. Thus, it is possible to carry out a single introduction, a continuous introduction or a stepwise introduction of the catalyst, the base, the olefine or the hydrogen peroxide.

A particular embodiment of the process according to the invention consists in keeping the reaction mixture substantially anhydrous. In this case, the concentration of water in the mixture is preferably kept below 2% of the weight of the latter. Very good results have been obtained when the reaction mixture contains less than 1% by weight of water.

In order to keep the mixture in the substantially anhydrous state, any water which happens to be present therein is removed continuously. Various techniques can be used for this purpose. In general, the water present in the reaction mixture is removed by vapourisation processes, such as distillation, azeotropic distillation or distillation by means of an inert gas.

If the water forms, with one of the constituents of the mixture, such as the solvent, a low boiling azeotrope, the boiling point of which is lower than that of the other constituents of the mixture and of the other possible azeotropes which could be formed, the water is generally removed by azeotropic distillation.

At least one azeotropic distillation agent which is different in nature from the reaction solvent can also be added to the reaction mixture. This agent is chosen from amongst those capable of forming, with water, a low boiling azeotrope, the boiling point of which is lower than that of the other constituents of the mixture and of the other possible azeotropes which could be formed. It is chosen to be inert towards the other constituents of the mixture, under the reaction conditions. Furthermore, it is chosen so as not to interfere with the homogeneity of the reaction mixture. Most frequently, it is chosen from amongst chlorohydrocarbons and aromatic hydrocarbons. Chlorohydrocarbons containing from 1 to 6 carbon atoms, and aromatic hydrocarbons optionally substituted by alkyl groups or halogens and containing from 6 to 12 carbon atoms, are suitable. Good results have been obtained with methylene chloride, chloroform, 1,2-dichloroethane, 1,2-dichloropropanes and benzene.

The distillation agent is used in variable amounts, the doses being chosen so as to maintain the homogeneity of the reaction mixture. In general, it is used at doses of not more than 50% and most frequently 30% of the weight of the reaction mixture. When an azeotropic distillation agent is used, it is generally used at doses of at least 1% and most frequently 3% of the weight of the reaction mixture.

This technique can advantageously be used when a reaction solvent is not used or when the water does not form, with the reaction solvent, a low boiling azeotrope, the boiling point of which is lower than that of the other constituents of the mixture and of the other possible azeotropes which could be formed.

Removal of the water by azeotropic distillation is very particularly suitable when the azeotrope thus formed is a heterogeneous azeotrope, because it is then possible to recycle the organic phase into the reaction mixture, after separation of the aqueous phase from the distillate.

If the boiling point of water is lower than that of the other constituents of the reaction mixture and of the possible azeotropes which could be formed, the process most frequently used is a distillation process or a process for distilling the water by the continuous passage of an inert gas into the reaction mixture. The latter technique is generally used when it is desired to avoid heating to the boil mixtures which are capable of decomposing at their boiling point.

According to another particular embodiment of the process according to the invention, the olefine is reacted with the hydrogen peroxide without continuous removal of the water present in the reaction mixture. In this case, the reaction mixture can advantageously be heated under reflux in order to remove the heat of reaction.

After reaction, the mixture can be subjected to various separation techniques, such as distillation and decantation, in order to collect the epoxide and the unconverted reactants, which can advantageously be recycled into the process.

The process according to the invention can be carried out continuously in an apparatus such as that shown schematically in the single FIGURE of the attached drawing, which relates to a particular practical embodiment.

A concentrated solution of hydrogen peroxide is introduced via 3 into a reactor 1 surmounted by a distillation column 2, and the organic solution containing the catalyst, the base and the olefine is introduced via 4. The olefine, the catalyst and the base are introduced via 5.

During the reaction, the water-solvent azeotrope leaves the distillation column 2 via 9, is condensed in the condenser 10 and is sent via 11 to the receiver 12. If the solvent has lower density than water, it is collected at the top of the receiver via 13, whilst the water is collected at the bottom of the receiver via 14; in the opposite case, the reverse applies. The solvent is recycled via 15 into the distillation column, where it constitutes the reflux. In certain cases, it is possible to send part of the solvent via 16 into the mixer 6, which is fed via 5 with olefine, base and catalyst.

Part of the reaction mixture is withdrawn continuously via 7 and subjected to successive separations in order to obtain, on the one hand, the unconverted olefine, which is sent back to 6, and, on the other hand, the epoxide, which constitutes the production.

Examples of the manufacture of epoxides (Examples 1, 4, 5, 8 and 9 to 13) are given below in order to illustrate the invention without thereby limiting its scope. Examples 2, 3, 6 and 7 are given by way of comparison.

EXAMPLE 1

Epoxidation of cyclohexene 100 ml of benzyl alcohol (966 millimols), 80 ml of cyclohexene (790 millimols), 0.45 ml of pyridine (5.6 millimols) and 200 mg of $SeO_2$ (1.8 millimols) are introduced successively into a glass reactor with a jacket, which is heated by oil circulation and fitted with a magnetic stirrer and a reflux condenser with a Florentine receiver, such as shown in FIG. 1. The Florentine receiver itself contains 20 ml of cyclohexene (198 millimols). After the reaction mixture has been heated to a temperature of 348 K., 10 ml of 84% strength $H_2O_2$ (340 millimols) are introduced over a period of 10 minutes. After the reaction has been left to proceed for a further 10 minutes, the cyclohexene oxide formed is determined by gas chromatography: 287 millimols.

The selectivity relative to $H_2O_2$ consumed is 86% (degree of conversion: 98%).

The productivity of cyclohexene oxide is 469 g/hour.liter of reaction mixture.

EXAMPLE 2

Epoxidation of cyclohexene 41 g of amyl alcohol, 39 mg of selenium dioxide (0.35 millimol), 0.3 g of disodium phosphate, $Na_2HPO_4$, and 41 g of cyclohexene (499 millimols) are introduced into a reactor fitted with a magnetic stirrer and a reflux condenser fitted with a Florentine receiver, such as that shown in FIG. 1. The Florentine receiver itself contains 20 ml of cyclohexene (198 millimols). This mixture is heated to a temperature of 354 K. and 5 ml of a 30% strength by weight aqueous solution of hydrogen peroxide (49.5 millimols) are introduced over a period of 12 minutes. The reaction is left to continue for 2 hours, the water being removed continuously by azeotropic distillation. The temperature is kept between 353 K. and 363 K.

The cyclohexene oxide formed is determined by gas chromatography: 7.6 millimols.

The selectivity relative to $H_2O_2$ consumed is 28% (degree of conversion: 55%).

The productivity of cyclohexene oxide is 3 g/hour.liter of reaction mixture.

EXAMPLE 3

Epoxidation of cyclohexene 41 g of amyl alcohol, 0.05 g of molybdenum oxide of the formula $MoO_3$ (0.34 millimol), 0.3 g of disodium phosphate, $Na_2HPO_4$, and 41 g of cyclohexene (499 millimols) are introduced into a reactor fitted with a magnetic stirrer and a reflux condenser fitted with a Florentine receiver. The Florentine receiver itself contains 20 ml of cyclohexene (198 millimols). This mixture is heated to a temperature of 354 K. and 5 ml of an 84% strength by weight aqueous solution of hydrogen peroxide (168 millimols) are introduced over a period of 12 minutes. The reaction is left to continue for 1 hour, the water being removed continuously by azeotropic distillation. The temperature is kept between 353 K. and 363 K.

The cyclohexene oxide formed is determined by gas chromatography: 3.9 millimols.

The selectivity relative to $H_2O_2$ consumed is 15% (degree of conversion: 41%).

The productivity of cyclohexene oxide is 3 g/hour.-liter of reaction mixture.

EXAMPLE 4

Epoxidation of 2-methylbut-2-ene 100 ml of benzyl alcohol, 100 ml of 2-methylbut-2-ene (944 millimols), 0.8 ml of quinoline (6.78 millimols), 250 mg of $SeO_2$ (2.25 millimols) and 5 ml of 84% strength $H_2O_2$ (170 millimols) are introduced successively into a glass reactor with a jacket, which is heated by oil circulation and fitted and with a magnetic stirrer and a reflux condenser with a Florentine receiver, such as shown in FIG. 1. The mixture is heated to the reflux temperature and 5 ml of 84% strength $H_2O_2$ (170 millimols) are added over a period of 5 minutes. The reaction is left to continue for a further 15 minutes and the isoamylene oxide formed is then determined: 272 millimols.

The selectivity relative to $H_2O_2$ consumed is 84% (degree of conversion: 95%).

The productivity of isoamylene oxide is 351 g/hour.-liter of reaction mixture.

EXAMPLE 5

Epoxidation of 2-methylbut-2-ene 100 ml of benzyl alcohol, 100 ml of 2-methylbut-2-ene (944 millimols), 0.8 ml of quinoline (6.78 millimols), 250 mg of $SeO_2$ (2.25 millimols) and 5 ml of 84% strength $H_2O_2$ (170 millimols) are introduced successively into a glass reactor with a jacket, which is heated by oil circulation and fitted with a magnetic stirrer and a reflux condenser without a Florentine receiver. The mixture is heated to the reflux temperature and 5 ml of 84% strength $H_2O_2$ (170 millimols) are added over a period of 5 minutes. The reaction is left to continue for a further 15 minutes and the isoamylene oxide formed is then determined: 269 millimols.

The selectivity relative to $H_2O_2$ consumed is 92% (degree of conversion: 87%).

The productivity of isoamylene oxide is 347 g/hour. liter of reaction mixture.

EXAMPLE 6

Epoxidation of 2-methylbut-2-ene 100 ml of n-butanol (1,093 millimols), 100 ml of 2-methylbut-2-ene (944 millimols), 1.09 ml of pyridine (13 millimols), 324 mg of $MoO_3$ (2.25 millimols) and 10 ml of 84% strength $H_2O_2$ (326 millimols) are introduced successively into a glass reactor with a jacket, which is heated by oil circulation and fitted with a magnetic stirrer and a reflux condenser with a Florentine receiver, such as shown in FIG. 1. The mixture is then heated under reflux for 1 hour and the isoamylene oxide formed is then determined by gas chromatography: 39 millimols.

The selectivity relative to $H_2O_2$ consumed is 66% (degree of conversion: 18%).

The productivity of isoamylene oxide is 17 g/hour.-liter of reaction mixture.

EXAMPLE 7

Epoxidation of 2-methylbut-2-ene 100 ml of isopropyl alcohol, 100 ml of 2-methylbut-2-ene (944 millimols), 0.315 ml of triethylamine (2.26 millimols), 290 mg of selenous acid (2.25 millimols) and 5 ml of 84% strength $H_2O_2$ (170 millimols) are introduced successively into a glass reactor with a jacket, which is heated by oil circulation and fitted with a magnetic stirrer and a reflux condenser without a Florentine receiver. The mixture is heated to the reflux temperature (314 to 315 K.) and 5 ml of 84% strength $H_2O_2$ (170 millimols) are added over a period of 5 minutes. After a reaction time of 1 hour, the isoamylene oxide formed is determined: 73 millimols.

The selectivity relative to $H_2O_2$ consumed is 100% (degree of conversion: 22%).

The productivity of isoamylene oxide is 31 g/hour.-liter of reaction mixture.

EXAMPLE 8

Epoxidation of 2-methylbut-2-ene 78 ml of n-butanol (852 millimols), 130 ml of 2-methylbut-2-ene (1,202 millimols), 1.87 ml of quinoline (15.9 millimols) and 208 mg of $SeO_2$ (1.9 millimols) are introduced successively into a reactor which is similar to that of Example 1 but is fitted with a small Vigreux column. After the reaction mixture has been heated to a temperature of 316 K., 20 ml of approximately 50% strength by weight $H_2O_2$ (354 millimols) are introduced over a period of 45 minutes. After the reaction has been left to continue for a further 26 minutes, the isoamylene oxide formed is determined by gas chromatography: 291 millimols.

The selectivity relative to $H_2O_2$ consumed is 91% (degree of conversion: 90%).

The productivity of isoamylene oxide is 102 g/hour.-liter of reaction mixture.

EXAMPLE 9

Epoxidation of alpha-pinene 48 ml of n-butanol (525 millimols), 152 ml of alpha-pinene (975 millimols), 1.15 ml of pyridine (14 millimols) and 807 mg of $SeO_2$ (7.3 millimols) are introduced successively into a reactor similar to that of Example 1. The Florentine receiver itself contains 25 ml of n-butanol (273 millimols). After the reaction mixture has been heated to a temperature of 323 K., 10 ml of 84% strength $H_2O_2$ (340 millimols) are introduced over a period of 25 minutes. After the reaction has been left to continue for a further 39 minutes, the alpha-pinene oxide formed is determined by gas chromatography: 292 millimols.

The selectivity relative to $H_2O_2$ consumed is 88% (degree of conversion: 98%).

The productivity of alpha-pinene oxide is 208 g/hour.liter of reaction mixture.

EXAMPLE 10

Epoxidation of styrene 55 ml of n-butanol (601 millimols), 145 ml of styrene (1,266 millimols), 1.12 ml of pyridine (14 millimols) and 572 mg of $SeO_2$ (5.2 millimols) are introduced successively into a reactor which is similar to that of Example 1 but is fitted with a small Vigreux column. The Florentine receiver itself contains 25 ml of n-butanol (273 millimols). After the reaction mixture has been heated to a temperature of 341 K., 10 ml of 84% strength $H_2O_2$ (340 millimols) are introduced over a period of 24 minutes. After the reaction has been left to continue for a further 47 minutes, the styrene oxide formed is determined by gas chromatography: 190 millimols.

The selectivity relative to $H_2O_2$ consumed is 63% (degree of conversion: 89%).

The productivity of styrene oxide is 120 g/hour.liter of reaction mixture.

EXAMPLE 11

Epoxidation of allyl alcohol 100 ml of allyl alcohol (1,470 millimols), 0.25 ml of pyridine (3.1 millimols), 450 mg of $SeO_2$ (4.1 millimols) and 10 ml of 84% strength $H_2O_2$ (340 millimols) are introduced successively into a glass reactor with a jacket, which is heated by oil circulation and fitted with a magnetic stirrer and a reflux condenser with a Florentine receiver, such as shown in FIG. 1. The reaction mixture is heated to a temperature of 343 K. under a pressure of 1.5 E+04 Pa. The reaction is left to continue for one hour, the olefin-water azeotrope which has condensed in the Florentine receiver being withdrawn and this volume being made up by the continuous addition of allyl alcohol (75 ml over a period of one hour). The glycidol formed is determined by gas chromatography: 284 millimols. The selectivity relative to $H_2O_2$ is 94% (degree of conversion: 82%).

The productivity of glycidol is 210 g/hour.liter of reaction mixture.

EXAMPLE 12

Epoxidation of 2,5-dihydrofuran 100 ml of 2,5-dihydrofuran (1,263 millimols), 0.38 ml of 2-chloropyridine (4.0 millimols), 450 mg of $SeO_2$ (4.1 millimols) and 10 ml of 84% strength $H_2O_2$ (340 millimols) are introduced successively into a glass reactor with a jacket, which is heated by oil circulation and fitted with a magnetic stirrer and a reflux condenser with a Florentine receiver, such as shown in FIG. 1. The Florentine receiver itself contains 25 ml of $CHCl_3$ (312 millimols). The reaction mixture is heated to a temperature of 337 K. and the reaction is left to continue for 1 hour.

The mixture collected in the Florentine receiver contains an aqueous phase, which is discarded, and an organic phase which is rich in chloroform and also contains 2,5-dihydrofuran, which is recycled into the reactor. The 3,4-epoxy-2,5-dihydrofuran formed is determined by vapour phase chromatography: 203 millimols.

The selectivity relative to $H_2O_2$ consumed is 76% (degree of conversion: 79%).

The productivity of epoxide is 175 g/hour.liter of reaction mixture.

EXAMPLE 13

Epoxidation of 2,5-dihydrofuran 100 ml of 2,5-dihydrofuran (1,263 millimols), containing 7% of $H_2O$, and 50 ml of benzen (559 millimols) are introduced into a separating funnel.

After decantation, the aqueous phase (3.5 ml) is removed. The organic phase is then transferred into a reactor with a jacket, which is heated by oil circulation and fitted with a magnetic stirrer and a reflux condenser with a Florentine receiver, such as that shown in FIG. 1. 0.15 ml of 2-chloropyridine (1.6 millimols), 450 mg of $SeO_2$ (4.1 millimols) and 2 ml of 84% strength $H_2O_2$ (68 millimols) are introduced successively into the reactor. The reaction mixture is heated to a temperature of 343 K. and 8 ml of 84% strength $H_2O_2$ (272 millimols) are introduced over a period of 10 minutes. The reaction is left to continue for 50 minutes, the water being removed continuously by azeotropic distillation. The 3,4-epoxy-2,5-dihydrofuran formed is determined by vapour phase chromatography: 253 millimols.

The selectivity relative to $H_2O_2$ consumed is 78% (degree of conversion: 95%).

The productivity of epoxide is 145 g/hour.liter of reaction mixture.

We claim:

1. A process for the manufacture of epoxides, comprising:
   reacting hydrogen peroxide with a compound containing an ethylenic double bond, in a homogenous liquid reaction mixture in which the concentration of water is kept below 10% by weight, containing a catalyst consisting essentially of a compound selected from the group consisting of selenium dioxide and selenous acid, and a base which is a member of the group consisting of pyridine, halogeno-substituted pyridine, amino-substituted pyridine, alkoxy-substituted pyridine, alkyl-substituted pyridine, quinoline, and isoquinoline.

2. Process according to claim 1, wherein the catalyst is selenium dioxide.

3. Process according to claim 1, wherein the catalyst is selenous acid.

4. Process according to claim 1, wherein the catalyst is used in amounts of between 0.05 and 25 g per liter of reaction mixture.

5. Process according to claim 1, wherein the base is chosen from amongst pyridine, chloropyridine, quinoline, isoquinoline and their derivatives substituted by one or more alkyl groups containing from 1 to 2 carbon atoms per alkyl group.

6. Process according to claim 1, wherein the base is used in amounts of between 0.1 and 10 mols per gram atom of metal in the catalyst.

7. Process according to claim 1, wherein the compound containing an ethylenic double bond is chosen from amongst acyclic or cyclic olefines containing from 2 to 20 carbon atoms and not containing more than 6 carbon atoms per ring.

8. Process according to claim 1, wherein the reaction is carried out in the presence of an inert organic solvent chosen from amongst primary, secondary or tertiary alcohols containing from 3 to 8 carbon atoms.

9. Process according to claim 1, wherein the compound containing the ethylenic double bond is an olefin, and the molar ratio of olefin to hydrogen peroxide is at least 0.9 and less than 10.

10. Process according to claim 1, wherein the compound containing the ethylenic double bond is an acyclic olefin or a cyclic olefin containing no more than 6 carbon atoms per ring.

11. Process according to claim 1, wherein the concentration of water in the reaction mixture is kept below 5 percent by weight.

12. Process according to claim 1, wherein the concentration of water in the reaction mixture is kept below 2 percent by weight.

13. Process according to claim 1, wherein the concentration of water in the reaction mixture is kept below 1 percent by weight.

14. Process according to claim 1, wherein the base employed is quinoline or pyridine.

15. Process according to claim 1, wherein the base has a pKa between 2.5 and 7.5.

16. Process according to claim 1, wherein the concentration of water in the reaction mixture is less than 5% by weight, the base is quinoline or pyridine, the catalyst is selenium oxide, and the hydrogen peroxide is introduced into the reaction mixture over a period of 10 minutes and the reaction of hydrogen peroxide with a compound containing an ethylenic double bond proceeds for a further 10 minutes.

17. Process according to claim 1, wherein the amino-substituted pyridine is a member of the group consisting of 2-aminopyridine, 3-aminopyridine, and 2,5-diaminopyridine.

18. Process according to claim 1, wherein the alkoxy-substituted pyridine is a member of the group consisting of 3-methyoxypyridine, and 4-methoxypyridine.

19. Process according to claim 1, wherein the alkyl-substituted pyridine is a member of the group consisting of picolines, lutidines, collidines, ethylpyridines, and propylpyridines.

20. Process according to claim 2, wherein the base is chosen from amongst pyridine, chloropyridine, quinoline, isoquinoline and their derivatives substituted by one or more alkyl groups containing from 1 to 2 carbon atoms per alkyl group.

21. Process according to claim 9 wherein the olefin is used in amounts between 1.5 and 5 mols per mol of hydrogen peroxide.

* * * * *